United States Patent [19]

Sweet et al.

[11] Patent Number: 5,013,547

[45] Date of Patent: May 7, 1991

[54] ANTICANCER DRUG - ANTIBODY CONJUGATES AND METHOD FOR PREPARING SAME

[75] Inventors: Frederick Sweet; Leonard O. Rosik, both of St. Louis County, Mo.

[73] Assignee: Erbamont, Inc., Dublin, Ohio

[21] Appl. No.: 307,644

[22] Filed: Feb. 7, 1989

[51] Int. Cl.$^5$ ...................... A61K 39/44; A61K 17/06
[52] U.S. Cl. .................... 424/85.91; 530/390; 530/391; 530/408; 530/409; 530/410
[58] Field of Search ................ 424/85.91; 530/390, 530/391, 408, 409, 410

[56] References Cited

U.S. PATENT DOCUMENTS

| | | |
|---|---|---|
| 4,543,211 | 9/1985 | Kato et al. ................ 530/390 |
| 4,671,958 | 6/1987 | Rodwell et al. ............ 424/85.91 |
| 4,680,338 | 7/1987 | Sundoro .................... 525/54.1 |

Primary Examiner—Jeffrey E. Russel
Assistant Examiner—Kay Kim
Attorney, Agent, or Firm—Thompson, Hine and Flory

[57] ABSTRACT

A drug-protein conjugate of the general formula (I):

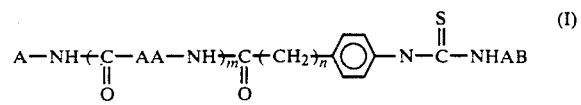

where the moiety A—NH— is the condensation product of an anticancer antibiotic having a free amino group, n is 0, 1 or 2, m is 0, 1, 2 or 3, the moiety —NHAB is the condensation product of a protein having a free amino group and the moiety

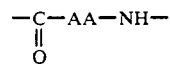

is the condensation product of an amino acid of the formula HOOC—AA—NH$_2$.

8 Claims, No Drawings

ANTICANCER DRUG - ANTIBODY CONJUGATES AND METHOD FOR PREPARING SAME

BACKGROUND

Chemotherapy with drugs conjugated to monoclonal antibodies appears promising because specific antibodies can be produced against well characterized and isolated, tumor-associated antigens. Because of the specificity of antibodies, this type of therapy is expected to reduce or eliminate the toxicity of currently used chemotherapeutic drugs. Following Kohler and Milstein's work with hybridomas that produce monoclonal antibodies (Kohler, G., and Milstein, C., "Continuous cultures of fused cells secreting antibody of predefined specificity," *Nature* 256, 495-497 (1975)) several monoclonal antibody-drug conjugates have been synthesized for treating a variety of murine and human tumors in vitro and in vivo.

Doxorubicin is active against ovarian cancer and its molecular structure has been well established. In 1975, Hurwitz, et al. first chemically modified the amino sugar ring of doxorubicin in attempts to link the drug to an antibody. Hurwitz, E., et al., "The covalent binding of daunomycin and Adriamycin to antibodies with retention of both drug and antibody activities," *Cancer Res.* 35, 1175-1181 (1975). Unfortunately, their use of sodium periodate which ruptures the sugar ring also causes other structural changes with concommitant loss of cytotoxic activity. Since these early efforts, the chemistry of linker technology has focused on utilizing the intact sugar group or the side chain at the C-9 position. Yang, H. M., and Reisfeld, R. A., "Doxorubicin conjugated with monoclonal antibody directed to a human melanoma-associated proteoglycan suppresses the growth of established tumor xenografts in nude mice," *Proc. Natl. Acad. Sci.* 85, 1189-1193 (1988). Pietersz, C. A., Smyth, M. J., and McKenzie, I.F.C., "Immunochemotherapy of a murine thyoma with the use of idarubicin monoclonal antibody conjugates," *Cancer Res.* 48, 926-9311 (1988).

The ideal drug-antibody conjugate will specifically transport the drug to the cancer cells and the targeted drug will exhibit its usual toxicity. Such an ideal set of conditions will increase the therapeutic index of the drug. The anthracycline antibiotics have the widest spectrum of antitumor activity of all present chemotherapeutic agents. Daunorubicin and doxorubicin show efficacy towards leukemias and solid tumors respectively. An accepted mechanism by which daunorubicin inhibits cell growth is associated with the intercalation of the drug in DNA which interferes with mitosis. A second mechanism of inhibition of cell growth is associated with the tendency of anthracyline antibiotics to generate free radicals that are capable of disrupting cell membranes and electron transport. Doxorubicin is employed in the most widely accepted chemotherapeutic regimen for treating ovarian carcinoma, namely, cisplatin-doxorubicincyclophosphamide.

U.S. Pat. No. 4,093,607 to Sela et al. (1978), relates generally to antitumor drug-antibody conjugates and more particularly to conjugates to anticancer antibiotics such as daunomycin and doxorubicin and antigen binding dimers derived by proteolytic digestion of an immumoglobulin containing an antibody specific to a tumor antigen.

SUMMARY OF THE INVENTION

A principal object of the present invention is to provide a drug-protein conjugate of the formula (I)

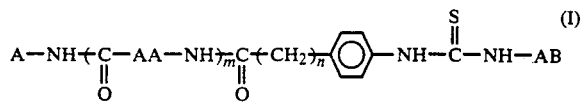

where the moiety A—NH— is the condensation product of an anticancer antibiotic having a free amino group, n is 0, 1 or 2, m is 0, 1, 2, or 3, the moiety —NHAB is the condensation product of a protein having a free amino group and the moiety

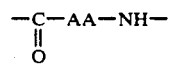

is the condensation product of an amino acid of the formula HOOC—AA—NH$_2$. Preferably, the moiety A—NH— is represented by the formula (II)

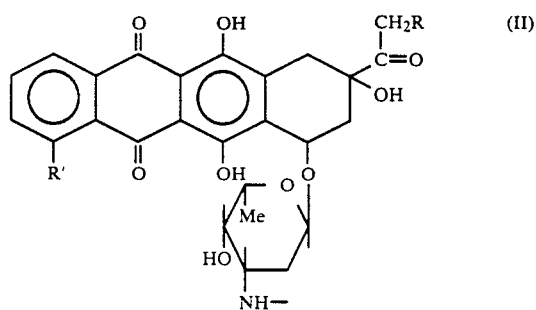

in which R is a hydrogen atom or a hydroxy group and R' is a methoxy group or a hydroxy group.

Another object of the present invention is to provide a method for preparing a drug-protein conjugate which comprises reacting an anticancer antibiotic or derivative thereof of the formula (III)

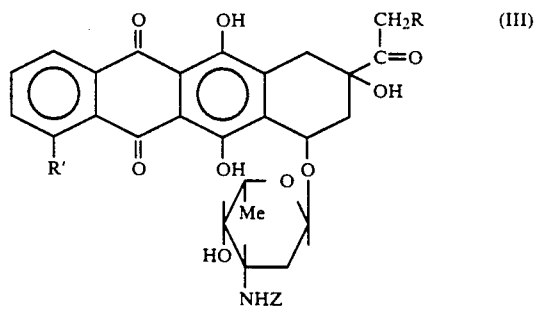

in which R is a hydrogen atom or a hydroxy group, R' is a hydroxy group or a methoxy group, and Z is a hydrogen atom or an amino acid chain of the formula

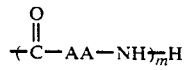

where m is 1, 2 or 3 with a compound of the formula (IV)

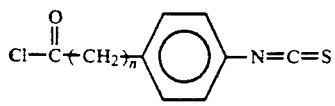

where n is 0, 1, or 2, such that the acid chloride moiety in the compound of formula (IV) condenses with the amino group in the amino sugar or the amino acid moiety in the compound of formula (III); and reacting the product of said reaction with a protein having a free amino group.

In accordance with the preferred embodiments of the invention the protein is a monoclonal antibody specific for a human tumor or other tissue malignancy and still more particularly ovarian carcinoma.

The present invention also provides intermediates useful in preparing drug-protein conjugates of the formula V:

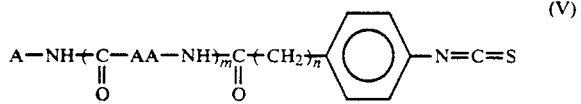

where A—NH, n, m and AA are defined as above. The intermediate of formula (V) is desirable because it is stable and can be simply mixed with a protein to prepare the drug conjugate. In most instances the isothiocyanate group reacts with free amino groups in the protein to bind the drug to the protein via a thiourea linkage. If the protein contains sulfhydryl groups, the isothiocyanate can also react with them to bind the drug via analogous linkage.

The present invention provides a method for treating a patient suffering from a tumor or tissue malignancy which comprises administering to the patient the aforementioned drug-antibody conjugate. The conjugate can be administered intravenously in amounts equivalent to the known anticancer antibiotics doxorubicin and daunomycin.

Finally, the drug-protein conjugation can also be useful in the laboratory to separate cells by selectively killing cells expressing the antigen for which the antibody is specific.

DETAILED DESCRIPTION OF THE INVENTION

In accordance with the present invention an anticancer antibiotic is modified such that it can be linked to a protein to form a drug-protein conjugate and, more particularly, a drug-antibody conjugate specific for a particular tumor cell or other malignancy. The resulting conjugate retains both the properties of the drug and the properties of the protein.

In accordance with the preferred embodiments of the invention doxorubicin-antibody conjugates are prepared. When this conjugate binds to cancerous tissue, the conjugate kills the cancerous cells. It is not clear that the drug moiety must be released from the antibody, however, when certain amino acid spacers are present (as when m is 1, 2 or 3 in formula (I) above), the cells are believed to enzymatically remove the spacer and release the drug. While any of a number of amino acid spacers may be used for this purpose, the amino acid leucine is preferred.

It has been found to be particularly effective to bind the drug to the protein/antibody via a thiourea linkage as the conjugates are stable in the blood serum for days and the reaction between the modified drug (formula (V)) and the antibody proceeds with good yield. In the case of the monoclonal antibody OC125, the drug is linked to the antibody in a molar ratio of about 5:1 which provides optimal cytotoxic activity. The conjugate appears to be about 100–1000 times more active than the drug itself making it possible to use the drug in chemotherapies at much lower dosage levels. The conjugate is suitable for administration intravenously.

The linkers which have been identified can generally be represented by the formula (IV)

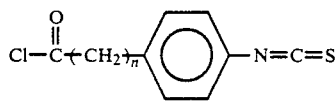

but it is anticipated that other linkers of the general formula (IVA)

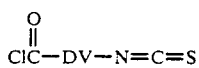

where DV is a divalent arylene, or arylene-alkylene bridge may also be useful.

Drug-antibody conjugates have been synthesized in which daunomycin (DNR) is attached via thiourea or analogous linkages to a mouse monoclonal anti-CA125 antibody (OC125), a nonspecific murine IgG$_1$, or to bovine serum albumin (BSA). DNR-OC125, DNR-IgG$^1$, and DNR-BSA conjugates are stable at physiological pH and 25° C. for several days. DNR-OC125 selectively killed dividing, but not nondividing populations of human ovarian cancer cell lines (SK-OV-3 or OVCAR-3) that express the CA125 antigen. However, at concentrations of the drug-antibody conjugate that are toxic to dividing cells the DNR-OC125 conjugate was not measurably toxic to nondividing cells of either SK-OV-3 or OVCAR-3 cell lines. Equivalent concentrations of the DNR-IgG$_1$ conjugate were neither toxic to the dividing nor the nondividing cells. The results suggest that the DNR-OC125 conjugates specifically kill the dividing cells which express CA125 due to antibody-antigen binding that concentrates the drug on the cancer cells. After the DNR-OC125 conjugates bind to the cancer cells they mediate the release of DNR which intercalates in DNA by a mechanism similar to that of the parent drug. The new DNR-OC125 conjugates may be useful for delivering DNR to ovarian tumors which express the CA125 antigen.

The syntheses of the new daunorubicin analogs are similar to those used for preparing amino nucleoside and steroid analogs that form stable conjugates with proteins. Samant, B. R., and Sweet, F. "5'-Bromoacetamido-5'deoxyadenosine: A novel reagent for labeling adenine nucleotide sites in proteins," *J. Biol. Chem.* 258, 12779 (1983). Sweet, F., and Murdock, G. L. "Affinity labeling of hormone-specific proteins," *Endoc. Rev.* 8, 154–184 (1987). The daunorubicin analogs formed stable conjugates with a monoclonal anti-OC125 antibody protein.

EXAMPLES

Cell lines. The cell line NIH: OVCAR-3 (OVCAR-3) was established in 1982. It was derived from the malignant ascites of a patient with progressive adenocarcinoma of the ovary, and is tumorigenic in nude mice. OVCAR-3 cells were maintained in RPM1-1640 medium supplemented with 10% fetal bovine serum (FBS, Hyclone Laboratories, Logan, Utah), 30 mg/mL L-glutamine (Sigma Chemical Company, St. Louis, Mo.), and 10 mg/mL of recombinant human insulin (Eli Lilly and Company, Indianapolis, Ind.). The cell line SK-OV-3 was established in 1973. It was derived from ascites fluid of a patient with adenocarcinoma of the ovary, and is tumorigenic in nude mice. SK-OV-3 cells were maintained in Dulbecco's modified Eagle's medium (DMEM) supplemented with 10% FBS and 30 mg/mL of L-glutamine. Cells were incubated at 37° C. in a humidified atmosphere of 95% air and 5% $CO_2$.

OVCAR-3 and SK-OV-3 cells were maintained as exponential monolayer cultures by passage twice a week. The cells were removed with 0.05% trypsin (GIBCO, Grand Island, N.Y.) in isotonic saline (buffered with phosphate at pH 7.2) (PBS) containing (0.045) mM EDTA (Sigma Chemical Company), and $2 \times 10^5$ cells were plated in 100 mm tissue culture dishes (Corning Glass Works, Corning, N.Y.).

The cell line B/C-N7.1C1 is a subclone of the continuous fibroblast cell line B/C-N which was originally derived from a BALB/c mouse fetus. B/C-N7.1C1 cells were grown in DMEM supplemented with 30 mg/mL of L-glutamine and 10% fetal calf serum.

Synthesis of daunorubicin analogs. Daunorubicin (DNR; from Wyeth Laboratories) was converted to three different analogs that were suitable for conjugation to OC125. Synthesis of the DNR analogs in each case used chemical methods that selectively utilized the 3'-amino group of the sugar moiety. Thus reactions of DNR with p-(isothiocyanato)-benzoyl (PIB) chloride or p-(isothiocyanato)phenyl-propionyl (PIPP) chloride provided the corresponding PIB-DNR or PIPP-DNR in 80 to 95% yields, following column chromatographic purification of the DNR analogs. The structural assignments of the DNR analogs were confirmed by NMR spectroscopy. The isothiocyanato group was incorporated in the structures of the DNR analogs because it is known to readily react with lysine (and other amino acid) residues in antibody proteins when the group is present. The chemistry of this reaction is similar to the reaction of fluorescein isothiocyanate (FITC); a popular reagent that forms stable conjugates with antibodies, making them fluorescent. Bromoacetyl (BA) bromide was similarly used to modify the 3'-amino group on the sugar moiety of DNR, providing the BA-DNR analog with the ability to form conjugates with antibody proteins. The BA group was selected because it had been successfully used to modify steroids and nucleosides so that the resulting analogs formed conjugates with enzyme and receptor protein [14].

Monoclonal antibody. OC125 is a murine $IgG_1$ that was developed against a human epithelial ovarian carcinoma cell line (OVCA433) established from a serous cystadenocarcinoma. OC125 is specific for a 220,000 molecular weight glycoprotein that is expressed on human epithelial ovarian cancer cells. The OC125 monoclonal antibody is available from Centocor Laboratories, Malverne, Pa.

Conjugation of DNR analogs with OC125 antibody. DNR analogs (PIB-DNR, PIPP-DNR, or BA-DNR) were mixed with OC125 (0.5 mg/mL) in saline buffered with phosphate at pH 8 in the dark at room temperature for 24 hours. Each DNR-OC125 conjugate was purified by dialysis to remove any unconjugated DNR. Then the amount of DNR conjugated to the OC125 antibody was calculated from measurements of DNR light absorbance at 490 nm and of the antibody protein concentration compared with an IgG protein standard. The calculated molar ratio of DNR to OC125 in the DNR-OC125 conjugates was generally between 3:1 and 4:1.

Growth inhibition of ovarian cancer cells with DNR-OC125 conjugates. Toxicity of DNR-OC125 conjugates to ovarian cancer cells in dividing and nondividing cell populations was determined by a radioactive chromium ($^{51}Cr$) uptake assay. Both dividing and nondividing cells were tested for toxicity of DNR-OC125 conjugates to quantitate the concentrations of the drug-antibody that are specifically toxic only to rapidly dividing cancer cells. To be effective, chemotherapy must be more toxic to rapidly dividing tumors cells than to quiescent normal cells. Although by definition the nondividing tumor cell populations are not normal cells, they can serve as "normal" controls because in vitro they behave similar to nondividing normal cells. Dividing ($2 \times 10^3$) and nondividing ($2 \times 10^5$) cells in 100 $\mu L$ of supplemented DMEM were plated into 96-well tissue culture plates and then incubated at 37° C. overnight, as described above. The next day, a 50 $\mu L$ solution was added to each well of various concentrations diluted in supplemented DMEM of: unmodified DNR (control); OC125 alone (control); unmodified DNR plus OC125 (control); DNR-OC125 conjugates (experimental). The nominal concentration of DNR in solutions of the DNR-OC125 conjugates was determined by measuring the light absorption of the solutions at 490 nm and calculating the concentrations from the molar extinction coefficient. Following two days of incubation, the degree of cytotoxicity was determined by measuring the $^{51}Cr$ uptake of the surviving cells.

$^{51}Cr$ uptake was determined by first washing the cells four times with medium and then incubating the washed cells with 30 $\mu L$ of PBS containing 50 $\mu Ci/mL$ of $^{51}Cr$, at 37° C. for 2 hours. The cells were washed four times with PBS and then lysed by addition of 150 mL of distilled water. The $^{51}Cr$ taken up by the cells was measured in a gamma counter. For both dividing and nondividing cell populations, the percent cytotoxicity was calculated with the following formula:

$$\text{Percent cytotoxicity} = \frac{\text{cpm incorporated by experimental}}{\text{cpm incorporated by control}} \times 100$$

The radioactivity incorporated by the control cells was 1,000 cpm to 1,200 cpm for dividing cells and 20,000 cpm to 24,000 cpm for nondividing cells in different experiments. Variation was less than 10% among triplicate samples from measurements of $^{51}Cr$ in each experiment.

Statistics. Incorporation of $^{51}Cr$ by dividing or nondividing cells and their corresponding controls was compared with Student's t-test for unpaired samples. The magnitude of cytotoxicity for experimental groups of dividing and nondividing cells was compared by the Delta method [26]. Values of $p < 0.05$ were considered significance.

RESULTS

Toxicity to ovarian cancer cells of daunorubicin-OC125 conjugates. The toxicity of the three DNR-OC125 conjugates for two human ovarian cancer cell lines (OVCAR-3 and SK-OV-3) was measured by a $^{51}$Cr uptake assay from which ID$_{50}$ values could be calculated. The ID$_{50}$ values for the toxicity of unmodified DNR or OC125 plus unmodified DNR towards the SK-OV-3 dividing cell populations was found to be in the range 0.5 to 0.6 $\mu$M. For similar cell populations, the ID$_{50}$ values for the toxicity of the BA-DNR-OC125 and PIPP-DNR-OC125 conjugates were 0.6 $\mu$M and 1.0 $\mu$M, respectively. On the basis of ID$_{50}$ values for the dividing cells, the DNR-OC125 conjugates essentially retain the toxicity of the parent drug. The ID$_{50}$ value is 40 $\mu$M for unmodified DNR with the nondividing cells. Because of their relatively low concentration, the toxic effects of the DNR-OC125 conjugates could not be tested at 40 $\mu$M on the nondividing cells. However, at 1.0 $\mu$M the DNR-OC125 conjugates had no measurable toxicity for the nondividing cells.

An ID$_{50}$ value of 30 $\mu$M was obtained for unmodified DNR or OC125 plus unmodified DNR for the OVCAR-3 dividing cell populations. None of the DNR-OC125 conjugates exhibited toxicity towards the dividing OVCAR-3 cells. The PIB-DNR-OC125 conjugate was much less toxic than that of the PIPP-DNR-OC125 conjugate for both cell lines. Thus only a 35% decrease in cell number was observed in the concentration range of 1.0 M to 2.0 $\mu$M when DNR attached to OC125 via the PIB linker.

Selective growth inhibition of ovarian cancer cells by DNR-OC125 conjugates. PIPP-DNR was conjugated to a nonspecific murine IgG$_1$ (PIPP-DNR-IgG$_1$) and also to bovine serum albumin (PIPP-DNR-BSA) to test the toxicity of DNR-protein conjugates which do not specifically bind to cancer cells that express the CA125 antigen. In the concentration range of 1.0 to 2.0 $\mu$M, neither the PIPP-DNR-IgG$_1$ nor PIPP-DNR-BSA exhibited measurable toxicity towards the dividing cells of OVCAR-3 or SK-OV-3 cell lines. Toxicity towards dividing cells with the PIPP-DNR-BSA conjugate was observed only at concentrations above 10 $\mu$M.

The drug conjugates PIPP-DNR-OC125, PIPP-DNR-IgG$_1$, and PIPP-DNR-BSA were tested for toxicity with dividing and nondividing cell populations of the B/C-N7.1C1 cell lines which does not express the CA125 antigen. PIPP-DNR-BSA and PIPP-DNR-IgG$_1$ at concentrations of 1.0. $\mu$M did not produce measurable growth inhibition of dividing or nondividing cells B/C-N7.1C1. At the 1.0 $\mu$M concentration, PIPP-DNR-IgG$_1$ produced 10% growth inhibition of the dividing B/C-N7.1C1 cells.

The BA-DNR-OC125 and PIPP-DNR-OC125 conjugates retained the toxicity of unmodified DNR towards dividing SK-OV-3 cancer cells, and to a lesser extent towards the OVCAR-3 cells. This pattern resembles the relative toxicity of unmodified DNR towards the two cell lines, in that, DNR had a ID$_{50}$ of 0.6 $\mu$M for dividing SK-OV-3 cells and a corresponding value of 30 $\mu$M for dividing OVCAR-3 cells.

The toxicity of BA-DNR-OC125 and PIPP-DNR-OC125 conjugates is highly specific for cancer cells which express the CA125 antigen as shown by the fact that they are not toxic for the B/C-N7.1C1 cells. Moreover, when DNR is conjugated to nonspecific murine IgG$_1$ or to bovine serum albumin the resulting conjugates because of their lack of binding specificity have greatly reduced toxicity for cancer cells that express the CA125 antigen.

The results imply that after the DNR-OC125 conjugates bind to cells which express the CA125 antigen, the cells mediate the release of DNR from the antibody. Analogous findings have been reported. By contrast, relative to the corresponding DNR-OC125 conjugates, concentrations of more than one order of magnitude of the PIPP-DNR-BSA or PIPP-DNR-IgG$_1$ conjugates are required to inhibit the growth of the cancer cells. Even then, the toxicity of PIPP-DNR-BSA and PIPP-DNR-IgG$_1$ is the same for both the dividing and nondividing cells. These results suggest that the mechanism of toxicity of the DNR-IgG$_1$ and DNR-BSA conjugates may have been mainly through free radical damage to cell membranes and/or interference with cellular electron transport.

The high degree of specificity in the toxicity of PIPP-DNR-OC125, and PIB-DNR-OC125 conjugates towards cancer cells expressing the CA125 antigen is interesting. At a nominal concentration of 1.0 $\mu$M of the DNR moiety, the three conjugates are specifically toxic to dividing SK-OV-3 cancer cells which express the CA125 antigen but not to either the nondividing SK-OV-3 cells or to the B/C-N7.1C1 cancer cells which do not express the antigen. This is underscored by experiments in which the PIPP-DNR-IgG$_1$ conjugate at a concentration of 1.0 $\mu$M is not toxic to dividing or nondividing cells of any cell line.

Because the conjugates of the present invention selectively kill cells, they can also be used in the laboratory as a means of cell separation.

Having described the invention in detail and by reference to preferred embodiments thereof, it will be apparent that modifications and variation are possible without departing from the scope of the invention defined in the appended claims:

What is claimed is:

1. A drug-protein conjugate of the general formula (I):

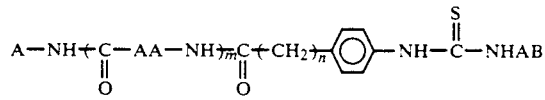

where the moiety A—NH— is the condensation product of an antibiotic having a free amino group; n is 0, 1 or 2; m is 1, 2 or 3; the moiety —NHAB is the condensation product of a protein having a free amino group; and the moiety

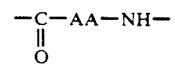

is the condensation product, of an amino acid of the formula HOOC—AA—NH$_2$.

2. The drug-protein conjugate of claim 1 wherein A—NH represents an anticancer antibiotic of the formula (II):

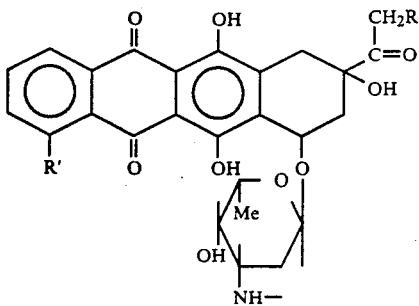

where R is hydrogen or hydroxy and R' is hydroxy or methoxy.

3. The drug-protein conjugate of claim 2 wherein said moiety —NHAB represents a monoclonal antibody having a free amino group and specific for a tumor or other tissue malignancy.

4. The drug-protein conjugate of claim 3 wherein said moiety A—NH— is daunomycin or doxorubicin.

5. The drug-protein conjugate of claim 4 wherein said antibody is an antibody specific for ovarian carcinoma.

6. The drug-protein conjugate of claim 5 wherein said antibody is OC125.

7. A method for treating a patient suffering from a tumor or other tissue malignancy which comprises administering to said patient a therapeutically effective amount of a drug-protein conjugate as defined is claim 1.

8. The drug-protein conjugate of claim 1 wherein said amino acid is leucine.

* * * * *